United States Patent [19]

Sanchez

[11] Patent Number: 5,177,278
[45] Date of Patent: Jan. 5, 1993

[54] PREPARATION OF CYCLODODECENE

[75] Inventor: Kathryn M. Sanchez, West Chester, Pa.

[73] Assignee: E. I. Du Pont de Nemours and Company, Wilmington, Del.

[21] Appl. No.: 781,362

[22] Filed: Oct. 23, 1991

[51] Int. Cl.$^5$ .................................................. C07C 5/02
[52] U.S. Cl. ...................................... 585/275; 585/273; 585/277
[58] Field of Search ........................ 585/275, 277, 273

[56] References Cited

U.S. PATENT DOCUMENTS 3,925,494  12/1975  Fahey ................................ 585/277

OTHER PUBLICATIONS

Fahey, Darryl R., "Selective Hydrogenation of 1,5,9-Cyclododecatriene to Cyclododecene Catalyzed by Ru Complexes" J. Org. Ch. 38(1) (1973) pp. 80-87.

Primary Examiner—Anthony McFarlane
Assistant Examiner—C. Everhart
Attorney, Agent, or Firm—Earl L. Handley

[57] ABSTRACT

Partial hydrogenation of 1,5,9-cyclododecatriene to form cyclododecene using ruthenium catalyst and a solvent selected from the group consisting of esters and ethers having a boiling point higher than 245 degrees C.

5 Claims, No Drawings

PREPARATION OF CYCLODODECENE

FIELD OF THE INVENTION

This invention relates to a process for the preparation of cyclododecene by the partial hydrogenation of 1,5,9-cyclododecatriene using a ruthenium ligand complex catalyst in a particular group of solvents.

BACKGROUND OF THE INVENTION

The preparation of cyclododecene by the partial hydrogenation of 1,5,9-cyclododecatriene using ruthenium ligand complex catalysts is disclosed in U.S. Pat. Nos. 3,925,494 and 3,804,914 to Fahey. The reaction is also disclosed in J. Ore. Chem., Vol. 38, No. 1, 1973, pages 80–86, by Darryl R. Fahey.

In the '914 patent the reaction is carried out in various solvents.

It is desirable to carry out the process in a solvent because it is easier to control the catalyst concentration in that the catalyst is not soluble enough in 1,5,9-cyclododecatriene at room temperature to give efficient result, and heating a mixture of catalyst and 1,5,9-cyclododecatriene to increase the solubility of the catalyst also increases the amount of by-product formed. Furthermore, the hydrogenation of 1,5,9-cyclododecatriene is an exothermic reaction, and it is difficult to control the temperature of the reaction in the absence of a solvent. The presence of the solvent acts as a "heat sink" for the reaction. Upon completion of the reaction the product, cyclododecene is separated from the reaction mixture.

An object of the present invention is to provide a process from the production of cyclododecene from 1,5,9-cyclododecatriene in which it is easy to control catalyst concentration, easy to control the exotherm, and easy to separate the product from the reaction mixture. In addition the process is readily employed in a continuous manner, by recycling the portion of the reaction mixture remaining after removal of cyclododecene.

SUMMARY OF THE INVENTION

The present invention is: in a process for the partial hydrogenation of 1,5,9-cyclododecatriene to cyclododecene which comprises contacting 1,5,9-cyclododecatriene, and a ruthenium ligand complex catalyst consisting essentially of $RuCl_2(CO)_2(PAr_3)_3$ and free triarylphosphine under hydrogenation conditions which partially reduce 1,5,9-cyclododecatriene to cyclododecene, the improvement which comprises dissolving the triene and the catalyst in a solvent selected from the group consisting of esters and ethers having a boiling point higher than 245 degrees C. that is inert under the hydrogenation conditions. The triarylphosphine ligand, $(PAr_3)$, is preferably selected from the group consisting of $P-(p-tolyl)_3$, $P-(p-F-C_6H_4)_3$, $P-(p-OMe-C_6H_4)_3$, and $P-(C_6H_5)_3$. The free triarylphosphine is usually the same as the ligand.

Also this invention is: A continuous process for the partial hydrogenation of 1,5,9-cyclododecatriene to cyclododecene which comprises forming a solution containing 1,5,9-cyclododecatriene, and a ruthenium ligand complex catalyst consisting essentially of $RuCl_2(CO)_2(PAr_3)_3$ and free triarylphosphine dissolved in a solvent having a boiling point higher than 245 degrees C., hydrogenating said triene to cyclododecene, recovering cyclododecene by distillation at reduced pressure, and returning the solvent containing the dissolved catalyst to the step of forming a solution containing 1,5,9-cyclododecatriene.

A preferred solvent for the invention is benzyl ether.

DETAILED DESCRIPTION

The process for the formation of cyclododecene from 1,5,9-cyclododecatriene is taught by the Fahey patents and publication referred to above. These patents and the publication are hereby incorporated by reference.

The amount of catalyst in the reaction mixture may vary widely, but it is usually in the range set forth in the Fahey patent '494, i.e. .0.00001 to about 0.5 mole of ruthenium-ligand complex per mole of 1,5,9-cyclododecatriene.

The process is normally operated at a pressure on the range of about 100 to about 600 psi and a a temperature in the range of about 130 to about 150 degrees C.

The amount of free triarylphosphine present in the reaction mixture should normally be in the range of about 0.5 to 10 wt. %.

Particular solvents that may be used include phenyl ether, benzyl benzoate, dioctyl phthalate, benzyl ether, and the dimethyl ester of adipic acid.

EXAMPLES

Example 1

$RuCl_2(CO)(PPh_3)_2$, 0.25 g and triphenylphosphine, 1.70 g were dissolved in 35 g of phenyl ether under nitrogen. The solution was transferred to the reactor. Cyclododecatriene, 100 g, was then added to the reactor. The reactor was heated under nitrogen to reaction temperature, 150° C. Hydrogen pressure, 500 psi was then added. Samples were withdrawn periodically for analysis by gas chromatography. Conversion to cyclododecene and cyclododecane at 4 hours was 75.17% with selectivity to cyclododecene at 97.11%.

Example 2

The same procedure as in Example 1 was followed using benzyl benzoate instead of phenyl ether as the solvent. Conversion to cyclododecene and cyclododecane at 4 hours was 78.89% with selectivity to cyclododecene at 96.71%.

Example 3

The same procedure as in Example 1 was followed using dioctyl phthalate as the solvent. Conversion to cyclododecene and cyclododecane at 3.9 hours was 71.51% with selectivity to cyclododecene at 97.61%.

Example 4

The same procedure as in Example 1 was followed using benzyl ether as the solvent. Conversion to cyclododecene and cyclododecane at 5 hours was 87.24% with selectivity to cyclododecene at 96.58%.

Example 5

The same procedure as in Example 4 was followed using benzyl ether as the solvent. Catalyst and benzyl ether were heated to 100° C. for 5 hours prior to reaction. Conversion to cyclododecene and cyclododecane at 4.12 hours was 90.08% with selectivity to cyclododecene at 96.08%.

Example 6

A catalyst run previously was recovered by distillation of the cyclododecene product out of the benzyl ether solution of catalyst and phosphine. The solution contained 35 g of benzyl ether, 0.18 g of catalyst, 1.3 g of triphenylphosphine. Cyclododecatriene, 100 g was added to this solution. The hydrogenation was performed as in Example 1, but at 300 psi hydrogen. Conversion to cyclododecene and cyclododecane at 3.62 hours was 86.31% with selectivity to cyclododecene at 96.52%.

Example 7

The same procedure as in Example 1 was followed using the dimethyl ester of adipic acid as the solvent. Conversion to cyclododecene and cyclododecane at 4.25 hours was 80.37% with selectivity to cyclododecene at 96.60%.

I claim:

1. In a process for the partial hydrogenation of 1,5,9-cyclododecatriene to cyclododecene which comprises contacting 1,5,9-cyclododecatriene, and a ruthenium ligand complex catalyst consisting essentially of $RuCl_2(CO)_2(PAr_3)_3$ and free triarylphosphine under hydrogenation conditions which partially reduce 1,5,9-cyclododecatriene to cyclododecene, the improvement which comprises dissolving the triene and the catalyst in a solvent selected from the group consisting of esters and ethers having a boiling point higher than 245 degrees C. that is inert under the hydrogenation conditions.

2. A continuous process for the partial hydrogenation of 1,5,9-cyclododecatriene to cyclododecene which comprises forming a solution containing 1,5,9-cyclododecatriene, and a ruthenium ligand complex catalyst consisting essentially of $RuCl_2(CO)_2(PAr_3)_3$ and free triarylphosphene dissolved in a solvent selected from the group consisting of esters and ethers having a boiling point higher than 245 degrees C., hydrogenating said triene to cyclododecene, recovering cyclododecene by distillation, and returning the solvent containing the dissolved catalyst to the step of forming a solution containing 1,5,9-cyclododecatriene.

3. The process of claim 1 in which the solvent is benzyl ether.

4. The process of claim 1 in which Ar is phenyl and the free triarylphosphine is triphenylphosphine.

5. The process of claim 1 in which the solvent is selected from the group consisting of phenyl ether, benzyl benzoate, dioctyl phthalate, benzyl ether and the dimethyl ether of adipic acid.

* * * * *